United States Patent [19]

Kludas et al.

[11] Patent Number: 4,464,362

[45] Date of Patent: Aug. 7, 1984

[54] TOPICAL SKIN REPAIR COMPOSITION

[75] Inventors: Martin Kludas; Dieter Heise, both of Berlin, Fed. Rep. of Germany

[73] Assignee: Estee Lauder Inc., New York, N.Y.

[21] Appl. No.: 355,579

[22] PCT Filed: Jun. 26, 1981

[86] PCT No.: PCT/EP81/00086

§ 371 Date: Feb. 23, 1982

§ 102(e) Date: Feb. 23, 1982

[87] PCT Pub. No.: WO82/00093

PCT Pub. Date: Jan. 21, 1982

[30] Foreign Application Priority Data

Jun. 27, 1980 [DE] Fed. Rep. of Germany ....... 3024318

[51] Int. Cl.$^3$ .............................................. A61K 35/74
[52] U.S. Cl. ...................................... 424/195; 424/95
[58] Field of Search ....................... 424/92, 93, 94, 95, 424/177, 180, 195

[56] References Cited

U.S. PATENT DOCUMENTS 4,057,627 11/1977 Stickl .................................... 424/92

FOREIGN PATENT DOCUMENTS

| | | |
|---|---|---|
| 2164052 | 7/1973 | Fed. Rep. of Germany . |
| 2617919 | 11/1976 | Fed. Rep. of Germany . |
| 2852779 | 6/1979 | Fed. Rep. of Germany . |
| 1096421 | 6/1955 | France . |
| 1112301 | 3/1956 | France . |
| 2052143 | 4/1971 | France . |
| 1603826 | 7/1971 | France .............................. 424/361 |
| 468290 | 7/1937 | United Kingdom . |
| 1545206 | 5/1979 | United Kingdom . |
| 2037160 | 7/1980 | United Kingdom . |

OTHER PUBLICATIONS

Winter, A Consumer's Dictionary of Cosmetic Ingredients, Crown Pub., N.Y., 1976, pp. 51, 159, 160.

Clark, Secrets of Health & Beauty, Jove/HBJ, N.Y. ©1969, 2nd Jove/HBJ printing Feb., 1979, pp. 16, 17, 104, 105, 158, 159.

Komeiji, Chem. Abs., vol. 87, 1977, Ab. No. 87: 141124b.

Yamashita, Chem. Abs., vol. 88, 1978, Ab. No. 88: 110537e.

Bergey's Manual of Determ. Bacti., Williams & Wilkins, Baltimore, Md., 8th Ed., 1974, pp. 576, 599, 633, 659, 660.

Davis et al., Microbiol., Harper-Row, Hagerstown, Md., 2nd Ed., 1973, pp. 783–802.

Frobisher et al., Fundamentals of Microbiol., W. B. Saunders, Phila., Pa., 9th Ed., 1974, pp. 72–85, 94, 95, 572–575, 577, 578, 580–582, 585, 586, 588.

*Primary Examiner*—Sam Rosen
*Attorney, Agent, or Firm*—Blum Kaplan Friedman Silberman & Beran

[57] ABSTRACT

Cosmetic compositions containing an active substance complex for promoting the DNA repair process of the skin cells, in order to guard against possible cellular skin damage due to excessive light influence, and to counteract the light-caused aging process of the skin. The active substance complex consists of inactivated cultures of bacteria of the genus Bifidobacterium or bacteria related to this genus.

20 Claims, No Drawings

TOPICAL SKIN REPAIR COMPOSITION

It is known that excessive exposure to solar radiation can cause chronic skin damage, which can lead to epidermal changes, such as atrophy, pigment displacements, collagenous degeneration up to permanent damage of the desoxyribonucleic acid (DNA) of the cells. The sequence of the elements of the double-stranded helix structure of the DNA, as is known, during cell division secures the correct replication of the genetically coded hereditary dispositions. Intensive exposure of the skin to UV radiation leads to a thymidine dimerisation by cycloaddition between two adjacent thymidine elements of the DNA. This change in the structure of the nucleic acid can lead to either the death of the cell or to inheritable cell damage.

Each cell, however, possesses a so-called endogenous repair system, consisting of an enzymatically controlled reaction sequence in order to cut the thymidine dimers out of the DNA strand and to replace these by thymidine monomers.

This natural DNA repair mechanism, above all, possesses only a limited capacity which is extensively exhausted by an excessive intense effect of light and sun. Moreover, it is known from investigations, (J. B. Little ("Gerontology" 22, 28–55 (1976)), that between the aging of a cell and its ability to permit the course of a normal repair process, there exists a close relationship wherein it still must be explained as to whether a reduction in the repair ability of the cell is the direct cause for the aging or it represents only an accelerating factor.

Accordingly, it is an object of the present invention to provide cosmetic compositions, the use of which allows to increase the body's own DNA repair capacity of the skin cells, reduced by excessive influence of light to the physiologically required level and in this manner preclude permanent cell damage and retard the light-caused aging process of the skin.

The foregoing object is achieved by local application of cosmetic compositions to the skin, the compositions containing an active substance complex which promotes the DNA repair process of the skin cells. Ascertained as being particularly suitable therefore is an active substance obtained from inactivated cultures of bacteria of the genus Bifidobacterium or related types which is capable of causing a desirable increase in the body's own repair capacity for the skin cells, the repair capacity of which has been reduced by the influence of light.

By the application of these cosmetic compositions permanent cell damage can be prophylactically counteracted and the light-caused aging process of the skin retarded, which imparts to these compositions a high practical value from the cosmetic viewpoint.

The inventive active substance complex which promotes the repair process consists, for example, of inactivated bacteria of the genus Bifidobacterium, such as the species Bifidobacterium longum (Reuter). These contain the cytoplasm fraction with enzymes, such as lactic acid dehydrogenase, phosphatases, phosphoketolases and transaldolases, and in addition murein and polysaccharides.

The inactivated cells, for example, can be obtained by rinsing anaerobically obtained surface cultures of bifido bacteria with physiological NaCl solution, centrifugation, resuspending in physiological NaCl solution and treating with ultrasound (20 KHz) whilst cooling in an ice-bath to 0° C. until all viable organisms are killed. For this a period of about 20 minutes is required for each 100 ml of the solution. For the inactivation of the cells there are also other known mechanical operating methods that can be used, e.g., J. R. Norris and D. D. Ribbons "Methods in Microbiology" Volume 5B, pages 1 though 54 (1971) Publishers: Academic Press, London and New York.

However, there can be also utilized as the starting material bacteria related to the genus Bifidobacterium, such as are listed, for example, in Bergery's Manual of Determinative Bacteriology, 8th Edition (1975), under Actinomycetaceae, Propionibacteriaceae, Lactobacillaceae and coryneform bacteria (refer to, among others, pages 576, 599, 633 and 659 to 660).

On the basis of extensive in vivo and in vitro test series, it has been discovered that the natural DNA repair rate can be significantly increased by exogenic supply of the active substance complex, incorporated into cosmetic compositions. In individual test series there have been achieved rates of increase of more than 100 percent.

The repair promoting effect of the active substance complex could be proved with the following series of experiments:

I. IN VITRO TEST SERIES ON mouse spleen cells
human lymphocytes and
human fibroblasts In analogous experiments, the corresponding cell material was suspended in a solvent, treated with the active substance complex of inactivated cultures of *Bifidobacterium longum* (Reuter) to be tested and irradiated with an UV-lamp at 254 nm. Serving as reference is a similarly treated control series which, however, did not contain the active substance.

In order to suppress the scheduled DNA replication, the so-called semi-conservative synthesis, hydroxyurea was added as inhibitory substance. The now only proceeding so-called unscheduled synthesis is a direct measure for the excision repair process.

After the irradiation each preparation had titrated $H^3$-thymidine added thereto. This radioactively marked thymidine replaces during the repair process the defective thymidine dimer. The incorporation rate of the $H^3$-thymidine into the DNA measurable by the marking is a parameter for the repair rate.

As a result it was determined that, in all instances, the active substance complex showed, against the controls, a significant increase of the incorporation rate of $H^3$-thymidine.

II. IN VIVO TEST SERIES ON RATS

The animals had the test substances applied on shaved areas of their backs; the active substance complex of inactivated cultures of *Bifidobacterium longum* (Reuter) itself and also cosmetic compositions with a content of 5% or 10% active substance complex. To relativate the results, corresponding blank substances were used too. As an absolute reference for the active and the blank substances served the similarly treated but non-irradiated areas of the rats.

Prior to the irradiation a test group of ten animals had applied at an interval of four hours 50 mg each of the test and the blank substances on the provided skin areas. Seventy two hours after the first substance application, there followed the UV-irradiation. A control group of ten animals remained unirradiated. After the irradiation, the animals of the test and control group were injected with a solution of $H^3$-thymidine and with the hydroxyurea for the suppression of the scheduled DNA synthesis. Sacrifice of the animals of all groups was carried out under ether anaesthesia twenty four hours after the irradiation. Also here the determined $H^3$-thymidine incorporation rate is a measure for the repair activity of the test substance.

As a result it was determined that the active substance complex evidenced a statistical significant increase in the repair capacity in comparison to the controls. A further important result was that the cosmetic composition with 10% of the repair promoting active substance complex evidenced a four times higher, and the cosmetic composition with a content of 5% a two times higher repair activity than the active substance complex itself.

The following formulations are exemplary embodiments of the invention.

EXAMPLE I

Cream O/W (oil-in-water) with 10% of a repair promoting active substance complex produced in accordance with the above particulars.

The following ingredients were utilized:

| (a) Cetyl stearyl alcohol | 9.0% |
|---|---|
| Sodium cetyl stearyl sulfate | 1.0% |
| Decylester of oleic acid | 10.0% |
| Lanoline anhydrous | 2.0% |
| Triglyceride of fractionated coconut oil fatty acids | 5.0% |
| Preservative | q.s. |
| (b) Distilled water | 57.7% |
| 70% solution of sorbitol | 5.0% |
| (c) Repair promoting active substance complex of inactivated cultures of Bifidobacterium longum (Reuter) | 10.0% |

The preparation of the composition is effected by initially melting the ingredient combination (a) and heating to about 70° C. and adding thereto the solution set forth under (b), heated to 70° C. The mixture is stirred further until the cream cools to about 35° C. Thereafter the component (c) is stirred in until it is homogenously distributed.

EXAMPLE II

Cream W/O (water-in-oil) with 10% of a repair promoting active substance complex produced in accordance with the above particulars.

The following ingredients were utilized:

| (a) Mixture of high-molecular esters, primarily mixed esters of pentaerythritol fatty acid esters and citric acid alcohol esters, and mineral fats | 20.0% |
|---|---|
| Decylester of oleic acid | 5.0% |
| Vegetable oil | 5.0% |
| White vaseline | 5.0% |
| Preservative | q.s. |
| (b) Distilled water | 55.0% |
| (c) Repair promoting active substance complex of inactivated cultures of Bifidobacterium longum (Reuter) | 10.0% |

The preparation of the composition was carried out according to the method indicated in Example I.

EXAMPLE III

Gel with repair promoting active substance complex.

| (a) Water, distilled, preserved | 50.0% |
|---|---|
| Carbopol 940 (polyacrylic acid) | 0.5% |
| Phenonip (preservative) | 0.3% |
| (b) Water, distilled, preserved | 28.2% |
| Triethanolamine | 1.0% |
| (c) Repair promoting active substance complex of inactivated cultures of Bifidobacterium longum (Reuter) | 20.0% |

The composition is prepared by dispersing with rapid stirring of combination (a) stirring thereinto the solution under (b), and subsequently the component (c).

EXAMPLE IV

Lotion with repair promoting active substance complex.

| (a) Ethanol, 96% v/v | 15.0% |
|---|---|
| (b) Water, distilled, preserved | 76.4% |
| Citric acid | 0.3% |
| Phenonip (preservative) | 0.3% |
| 1.2 propylene glycol | 3.0% |
| (c) Repair promoting active substance complex | 5.0% |

The composition is prepared by making up a solution from the ingredients under (b). Thereafter, component (a) is added and then component (c).

We claim:

1. Cosmetic compositions for topical application to a person's skin for promoting the repair of DNA in skin cells damaged by exposure to ultraviolet radiation, comprising a vehicle for topical application and a DNA repair capacity effective amount of an active substance complex which promotes the DNA repair process in skin cells, the active substance complex including inactivated cultures of bacteria selected from a genus of the group consisting of Bifidobacterium, Actinomycetaceae, Propionibacteriaceae, Lactobacillaceae and Coryneform bacteria.

2. The cosmetic composition of claim 1, wherein the active substance complex is present in an amount of at least about 5 weight percent, based on the total weight of the composition.

3. The cosmetic composition of claim 1, wherein the active substance complex is present in an amount between about 5 and 20 weight percent, based on the total weight of the composition.

4. A cosmetic composition for topical application to a person's skin for promoting the repair of DNA in skin cells damaged by exposure to ultraviolet radiation, comprising a vehicle for topical application and a DNA repair capacity effective amount of an active substance complex including inactivated cultures of bacteria of the genus Bifidobacterium.

5. The cosmetic composition of claim 4, wherein the active substance complex is present in an amount of at least about 5 weight percent, based on the total weight of the composition.

6. The cosmetic composition of claim 4, wherein the active substance complex is present in an amount between about 5 to 20 weight percent, based on the total weight of the composition.

7. A cosmetic composition for topical application to a person's skin for promoting the repair of DNA in skin cells damaged by exposure to ultraviolet radiation, comprising a vehicle for topical application and a DNA repair capacity effective amount of an active substance complex including inactivated cultures of bacteria of the species *Bifidobacterium longum* (Reuter).

8. The cosmetic composition of claim 7, wherein the active substance complex is present in an amount of at least about 5 weight percent, based on the total weight of the composition.

9. The cosmetic composition of claim 7, wherein the active substance complex is present in an amount between about 5 to 20 weight percent, based on the total weight of the composition.

10. A method for promoting the repair of DNA of skin cells damaged by exposure to ultraviolet radiation, comprising applying to the skin a topical cosmetic composition including a vehicle for topical application and a DNA repair capacity effective amount of an active substance complex including inactivated cultures of bacteria of a genus selected from the group consisting of Bifidobacterium, Actinomycetaceae, Propionibacteriaceae, Lactobacillaceae and Coryneform bacteria.

11. The method of claim 10, wherein the active substance complex is present in amounts of at least about 5 weight percent, based on the total weight of the composition.

12. A method for promoting the repair of DNA of skin cells damaged by exposure to ultraviolet radiation, comprising applying to the skin a topical cosmetic composition including a vehicle for topical application and a DNA repair capacity effective amount of an active substance complex including inactivated cultures of bacteria selected from the genus Bifidobacterium.

13. The method of claim 12, wherein the active substance complex is present in amounts of at least about 5 weight percent, based on the total weight of the composition.

14. A method for promoting the repair of DNA of skin cells damaged by exposure to ultraviolet radiation, comprising applying to the skin a topical cosmetic composition including a vehicle for topical application and a DNA repair capacity effective amount of an active substance complex including inactivated cultures of bacteria of the species *Bifidobacterium longum* (Reuter).

15. The method of claim 14, wherein the active substance complex is present in an amount of at least about 5 weight percent, based on the total weight of the composition.

16. A method of preparing an active substance complex for promoting the repair of DNA in skin cells damaged by exposure to ultraviolet radiation, comprising inactivating cells of an anaerobically obtained surface culture of bacteria selected from a genus of the group consisting of Bifidobacterium, Actinomycetaceae, Propionibacteriaceae, Lactobacillaceae and Coryneform bacteria said inactivating of cells being by the steps of rinsing, resuspending, and subjecting the cells to ultrasound or mechanical inactivation.

17. The method of claim 16, including the steps of rinsing the bacteria with physiological NaCl solution, centrifuging the rinsed bacteria, resuspending the bacteria in physiological NaCl solution and subjecting the bacteria to ultrasound while cooling to 0° C.

18. An active substance complex for accelerating the repair of DNA in a person's skin cells damaged by exposure to ultraviolet radiation by topical application to the person's skin, comprising inactivated bacteria of a genus selected from the group consisting of Bifidobacterium, Actinomycetaceae, Propionibacteriaceae, Lactobacillaceae and Coryneform bacteria said bacteria being inactivated by rinsing, resuspending, and subjecting the bacterial cell to ultrasound or mechanical inactivation.

19. An active substance complex for accelerating the repair of DNA in a person's skin cells damaged by exposure to ultraviolet radiation by topical application to the person's skin, comprising inactivated bacteria of the genus Bifidobacterium said bacteria being inactivated by rinsing, resuspending, and subjecting the bacterial cell to ultrasound or mechanical inactivation.

20. An active substance complex for accelerating the repair of DNA in a person's skin cells damaged by exposure to ultraviolet radiation by topical application to the person's skin, comprising inactivated bacteria of the species *Bifidobacterium longum* (Reuter) said bacteria being inactivated by rinsing, resuspending, and subjecting the bacterial cell to ultrasound or mechanical inactivation.

* * * * *